US010767054B2

(12) United States Patent
Sayah et al.

(10) Patent No.: US 10,767,054 B2
(45) Date of Patent: Sep. 8, 2020

(54) PROCESS FOR PREPARING INDIGO CARMINE

(71) Applicant: PROVEPHARM LIFE SOLUTIONS, Marseilles (FR)

(72) Inventors: Babak Sayah, Marseilles (FR); Stéphane Queru, Marseilles (FR); Michel Feraud, Marseilles (FR); Nicolas Lopez, Marseilles (FR)

(73) Assignee: PROVEPHARM LIFE SOLUTIONS, Marseilles (FR)

( * ) Notice: Subject to any disclaimer, the term of this patent is extended or adjusted under 35 U.S.C. 154(b) by 0 days.

(21) Appl. No.: 16/465,040

(22) PCT Filed: Nov. 27, 2017

(86) PCT No.: PCT/FR2017/053260
§ 371 (c)(1),
(2) Date: May 29, 2019

(87) PCT Pub. No.: WO2018/100277
PCT Pub. Date: Jun. 7, 2018

(65) Prior Publication Data
US 2019/0292370 A1  Sep. 26, 2019

(30) Foreign Application Priority Data
Dec. 1, 2016  (FR) .................................... 16 61784

(51) Int. Cl.
*A23L 5/47*    (2016.01)
*A61K 47/22*   (2006.01)
*C09B 67/54*   (2006.01)
*C09B 7/02*    (2006.01)

(52) U.S. Cl.
CPC ................. *C09B 7/02* (2013.01); *A23L 5/47* (2016.08); *A61K 47/22* (2013.01); *C09B 67/0096* (2013.01); *A23V 2002/00* (2013.01)

(58) Field of Classification Search
CPC ....... C09B 7/02; C09B 67/0096; A61K 47/22; A23L 5/47; A23V 2002/00
See application file for complete search history.

(56) References Cited

U.S. PATENT DOCUMENTS

| 647,280 A | 4/1900 | Sandmeyer |
| 2014/0155625 A1 | 6/2014 | Birau et al. |
| 2020/0017689 A1 | 1/2020 | Pullagurla et al. |

FOREIGN PATENT DOCUMENTS

| DE | 180 097 C | 12/1903 | |
| DE | 274 287 5 A1 | 4/1979 | |
| DE | 2742875 A1 * | 4/1979 | ............. G01N 33/84 |
| JP | 2012/188518 A | 10/2012 | |
| JP | 5449167 B2 | 3/2014 | |
| RU | 1793717 C | 1/1996 | |
| WO | 2010/018723 A1 | 2/2010 | |
| WO | 2011/016487 A1 | 2/2011 | |
| WO | 2011/026109 A1 | 3/2011 | |
| WO | 2011/107945 A1 | 9/2011 | |
| WO | 2014/001050 A1 | 1/2014 | |
| WO | 2015/114548 A1 | 8/2015 | |
| WO | 2015/130539 A1 | 9/2015 | |
| WO | 2018/116325 A1 | 6/2018 | |

OTHER PUBLICATIONS

Fuhrhop et al. Langmuir 1990, 6, 497-505. (Year: 1990).*
Stockert Acta Histochem. 1994, 96, 8-14. (Year: 1994).*
Guange et al. Huagong Xuego 2010, 61, 923-928. (Year: 2010).*
Guange et al. Huagong Xuego 2010, 61, 923-928 Partial Machine Translation from Google Translate (generated on Apr. 17, 2020) (Year: 2020).*
"Scientific Opinion on the re-evaluation of Indigo Carmine (E 132) as a food additive;" EFSA Journal; 2014; pp. 1-51; vol. 12, No. 7.
Kim et al.; "Hypotension in patients administered indigo carmine containing impurities—A case report;" Korean J. Anesthesiol.; 2011; pp. 435-438; vol. 61, No. 5.
Capron, F.; Blues and carmines of indigo: a practical treatise on the fabrication of every commercial product dervied from indigo; 1863; Philadelphia: H.C. Baird. <https://catalog.hathitrust.org/Record/006218585>.
Carraher et al.; "Organotitanium Polydyes Derived from Phenylsulfonphthalein Dyes, and Congo Red, Eriochrome Black T, Nigrosine and Indigo Carmine-Synthesis and Doping Characteristics;" Journal of Macromolecular Science: Part A—Chemistry: Pure and Applied Chemistry; 2006; pp. 773-785; vol. A15, No. 5.
R.W. Sabnis; Handbook of Biological Dyes and Stains—Synthesis and Industrial Applications; 2010; p. 239; Wiley and Sons.
Shadi et al.; "Analysis of the conversion of indigo into indigo carmine dye using SERRS;" ChemComm; 2004; pp. 1436-1437.
ICH harmonised tripartite guideline—Impurities in new drug substances—Q3A(R2); Step 4 version; International Conference on Harmonisation of Technical Requirements for Registration of Pharmaceuticals for Human Use; 2006.
Baltac et al.; "The Synthesis of Some Food Dyes for Natural and Synthetic Fibres;" Rev. Chim; 2012; pp. 618-620; vol. 63, No. 6.
Bianda et al.; "Colorful Experiments for Students: Synthesis of Indigo and Derivatives;" Chemistry: Bulgarian Journal of Science Education; 2013; pp. 52-65; vol. 22, No. 1.
Feb. 28, 2018 Search Report issued in International Application No. PCT/FR2017/053260.
Dec. 31, 2019 Office Action issued in U.S. Appl. No. 16/471,999.
Steingruber, E., "Indigo and Indigo Colorants", Ullmann's Encyclopedia of Industrial Chemistry:Wiley InterScience, (Aug. 2004), pp. 1-10.

(Continued)

*Primary Examiner* — Amanda L. Aguirre
(74) *Attorney, Agent, or Firm* — Oliff PLC

(57) ABSTRACT

Process for preparing disodium 5,5'-indigosulfonate, the feedstock being indigo, this process including the following steps: i) the indigo is subjected to a sulfonation treatment resulting in a mixture that contains 5,5'-indigosulfonic acid, this process including: ii) a reduction treatment is applied to the mixture obtained in step i), and optionally a purification step, so as to obtain a composition including leuco-5,5'-indigosulfonic acid, iii) the leuco-5,5'-indigosulfonic acid is isolated from the composition resulting from step ii), iv) the leuco-5,5'-indigosulfonic acid resulting from step iii) is oxidized to give disodium 5,5'-indigosulfonate.

15 Claims, No Drawings

(56) References Cited

OTHER PUBLICATIONS

Feb. 22, 2018 International Search Report issued in International Patent Application No. PCT/IN2017/050615.
Leclerc, S. et al., "Indirubins Inhibit Glycogen Synthase Kinase-3b and CDK5/P25, Two Protein Kinases Involved in Abnormal Tau Phosphorylation in Alzheimer'S Disease", Journal of Biological Chemistry, vol. 276, No. 1, (2001), pp. 251-260.

* cited by examiner

PROCESS FOR PREPARING INDIGO CARMINE

The present invention relates to a novel process for preparing the indigo carmine molecule, this process making it possible to achieve a high degree of purity, while at the same time being very simple to perform and having high yields.

PRIOR ART

Indigo carmine, also known under the names disodium 5,5'-indigosulfonate and disodium 3,3'-dioxo-2,2'-bis(indolidene)-5,5'-disulfonate (CAS number 860-22-0), is known for its uses as a dye, in the food, pharmaceutical and cosmetics fields, but also in the fields of printing and photography (R. W. Sabnis, Handbook of Biological Dyes and Stains, 2010, Wiley and Sons, page 239). In the food sector, indigo carmine is the subject of specifications which are reported in EFSA Journal 2014; 12(7): 3768. In the pharmaceutical sector, it is used notably for dying tissues, for the detection of certain tumoral cells. Disodium 5,5'-indigosulfonate is generally obtained from indigo

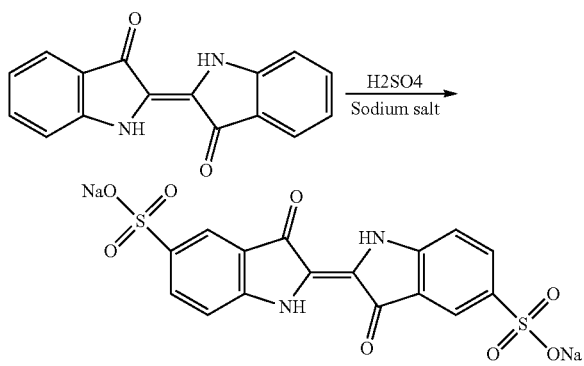

or 2-(1,3-dihydro-3-oxo-2H-indol-2-ylidene)-1,2-dihydro-3H-indol-3-one (CAS number: 482-89-3), according to a reaction summarized in scheme 1 below:

Scheme 1

However, in the course of this reaction, other compounds are usually formed that are mono-, di-, tri- or tetrasulfonated, predominantly in positions 5, 5', 7, 7'.

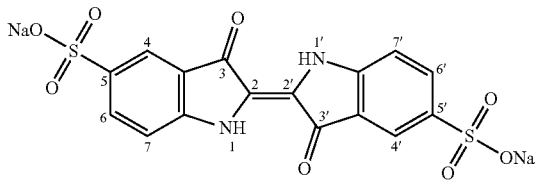

Disodium 5,5'-indigosulfonate

The disulfonated isomers are present in large amounts, and their physicochemical properties are very similar to those of indigo carmine. The structural similarity of the disulfonated molecules makes them difficult to separate. The presence of disulfonated isomers has the drawback, for medical or diagnostic applications, of introducing undesired contaminants into the patient's body. Sung-Hoon Kim et al., Korean J. Anesthesiol. 2011 November; 61(5): 435-438 have described cases of hypotension in the case of patients to whom an indigo carmine containing impurities had been administered. These side effects were attributed to the impurities.

The object of the invention was thus to develop a process for preparing disodium 5,5'-indigosulfonate that is substantially free of impurities, and notably of disulfonated impurities. It was sought to develop a process which gives access to a disodium 5,5'-indigosulfonate which complies with the EFSA requirements in the food sector and with the standard ICH in the pharmaceutical sector (International conference on harmonisation of technical requirements for registration of pharmaceuticals for human use; ICH harmonised tripartite guideline—Impurities in new drug substances—Q3A (R2); Step 4 version; 25 Oct. 2006). The ICH standard specifies that an active principle should not contain unidentified impurities in a content of greater than or equal to 0.10% relative to the active principle. It was sought to develop a process that is rapid, inexpensive, efficient, with high yields, and readily extrapolable to the industrial scale.

SUMMARY OF THE INVENTION

The invention relates to a process for preparing disodium 5,5'-indigosulfonate, the starting material being indigo, this process comprising the following steps:

i) indigo is subjected to a sulfonation treatment leading to a mixture which contains 5,5'-indigosulfonic acid, this process being characterized in that:

ii) the mixture obtained in step i) is subjected to a reduction treatment, and optionally a purification step, so as to obtain a composition comprising leuco-5,5'-indigosulfonic acid, iii) the leuco-5,5'-indigosulfonic acid is isolated from the composition derived from step ii), iv) the leuco-5,5'-indigosulfonic acid derived from step iii) is oxidized to disodium 5,5'-indigosulfonate.

According to a preferred embodiment, the reduction treatment of step i) is performed using sodium dithionite in aqueous medium.

According to a preferred embodiment, the leuco-5,5'-indigosulfonic acid precipitates from the reaction medium on conclusion of step ii).

According to a preferred embodiment, step iii) includes at least one step consisting in:

iiia) filtration of the composition derived from step ii), iiib) recovery of the solid retained on the filter.

Advantageously, step iii) also includes, after step iiib), at least one step iiic) consisting in washing the solid with an aqueous medium.

More advantageously, step iiic) is applied from one to five times.

According to a preferred embodiment, the composition obtained on conclusion of step iii) includes at least 90 mol % of leuco-5,5'-indigosulfonic acid relative to the total number of moles of the composition.

According to a preferred embodiment, step iv) includes at least one step iva) consisting of a treatment with a base in alcoholic medium in the presence of an oxidizing agent.

Advantageously, step iva) consists of a treatment with sodium ethoxide in ethanol, in the presence of an oxidizing agent.

Advantageously, the oxidizing agent is gaseous oxygen.

According to a preferred embodiment, the process also includes, after step iva), at least one step ivb) consisting of one or more washes with one or more alcoholic and/or aqueous-alcoholic solvents.

The invention also relates to the use of the process defined above for producing a composition comprising at least 99.5% of disodium 5,5'-indigosulfonate, the percentage being measured by high-pressure liquid chromatography with detection at 290 nm.

The invention also relates to the use of the process as defined above for producing a composition in which no impurity is present in an amount of greater than 0.10%, the percentage being measured by high-pressure liquid chromatography with detection at 290 nm.

The invention also relates to a process for manufacturing a medicament or a diagnostic product comprising disodium 5,5'-indigosulfonate, this process comprising the manufacture of disodium 5,5'-indigosulfonate via the process described above and detailed below, and the introduction of the disodium 5,5'-indigosulfonate into a pharmaceutically acceptable support.

The invention also relates to a process for manufacturing a food composition comprising disodium 5,5'-indigosulfonate, this process comprising the manufacture of disodium 5,5'-indigosulfonate via the process described above and detailed below, and the introduction of the disodium 5,5'-indigosulfonate into a support that is compatible with a food application.

For example, the latter process may concern the manufacture of a food coloring composition, or of a colored food composition.

The inventors have observed, surprisingly, that leuco-5,5'-indigosulfonic acid could be readily separated from its disulfonated isomers, obtained by sulfonation of indigo and application of a reduction treatment, whereas mixtures of 5,5'-indigosulfonic acid and its disulfonated isomers, in acid form or in disodium salt form, are difficult to separate.

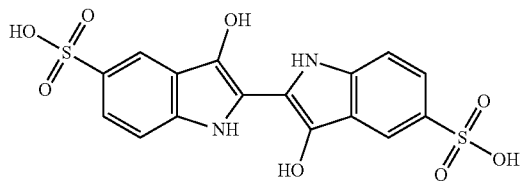 [SMILES: O=S(=O)(O)c1ccc2[nH]c(-c3[nH]c4ccc(S(=O)(=O)O)cc4c3O)c(O)c2c1]

Leuco-5,5'-indigosulfonic Acid

Specifically, the reduction was performed in a reaction medium in which leuco-5,5'-indigosulfonic acid is sparingly soluble, whereas its contaminants, notably its disulfonated isomers, are soluble in this medium.

Proceeding via these intermediate products in reduced form thus allows efficient separation, with high yields. Leuco-5,5'-indigosulfonic acid is thus recovered. The isolated product may then be subjected to an oxidation treatment so as to form a disodium 5,5'-indigosulfonate having a high level of purity.

DETAILED DESCRIPTION

Step i): Sulfonation of Indigo

The starting material is indigo or 2-(1,3-dihydro-3-oxo-2H-indole-2-ylidene)-1,2-dihydro-3H-indole-3-one (CAS: 482-89-3). Indigo is subjected to a sulfonation

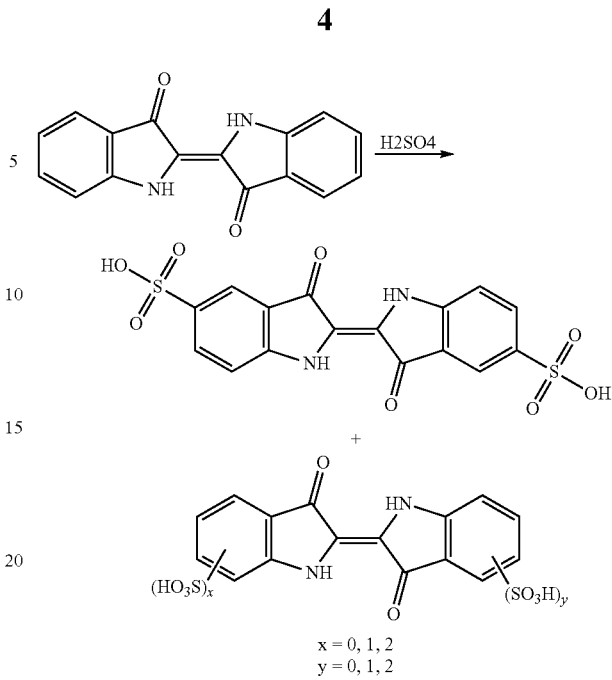

treatment according to scheme 2 below:

Scheme 2: Sulfonation Reaction of Indigo

This known reaction is usually performed by treatment with sulfuric acid. Reference may be made, for example, to the following publications: U.S. 647280; Tudora Baltac et al., Revista de Chimie (Bucharest, Romania) (2012), 63(6), 618-620; Iqbal T. Shadi et al., Chemical Communications (Cambridge, United Kingdom) (2004), (12), 1436-1437; Capron, F. (1863), Blues and carmines of indigo: a practical treatise on the fabrication of every commercial product derived from indigo; Philadelphia: H. C. Baird (https://catalog.hathitrust.org/Record/006218585); Vanessa Bianda et al., Bulgarian Journal of Science Education, Volume 22, Number 1, 2013; Charles E. Carraher et al., Journal of Macromolecular Science, Volume 15, Issue 5 1981, pages 773-785; R. W. Sabnis, Handbook of Biological Dyes and Stains, 2010, Wiley and Sons, page 239.

However, the process of the invention is not limited to the product of this reaction and can be applied to any composition comprising 5,5'-indigosulfonic acid and disulfonated isomers of 5,5'-indigosulfonic acid, irrespective of the process for obtaining them.

When the starting composition is derived from the sulfonation of indigo, it may also comprise, in addition to 5,5'-indigosulfonic acid and disulfonated isomers: indigo, monosulfonated, trisulfonated, tetrasulfonated derivatives, and also side products of this reaction. However, usually, these other derivatives are removed by means of a known method, for instance high-pressure liquid chromatography (HPLC).

When the starting composition is derived from the sulfonation of indigo, it comprises approximately from 60% to 95% of 5,5'-indigosulfonic acid and from 5 to 40% of disulfonated isomers, preferably from 75 to 80% of 5,5'-indigosulfonic acid and from 20 to 25% of disulfonated isomers, the percentages being given as number of moles relative to the sum of the numbers of moles of all of the disulfonated molecules. However, the process of the invention may be applied to a composition comprising a mixture of isomers in all proportions.

Advantageously, for implementation in the process of the invention, use is made of a starting composition in which 5,5'-indigosulfonic acid and its disulfonated isomers represent at least 90 mol % relative to the total number of moles of the starting composition, even more advantageously at least 95%, and better still at least 98%.

The term "disulfonated isomers" of 5,5'-indigosulfonic acid means any molecule having the structure of indigo, or 2-(1,3-dihydro-3-oxo-2H-indol-2-ylidene)-1,2-dihydro-3H-indol-3-one, bearing a substitution with a sulfonic acid or sulfonate function on each of the indole groups. 5,7'-indigosulfonic acid is an example of a disulfonated isomer of 5,5'-indigosulfonic acid.

Step ii): Reduction of the Mixture Derived from Step i)

In a first step, the mixture derived from step i) comprising 5,5'-indigosulfonic acid is subjected to a reduction treatment leading to a mixture of leuco-5,5'-indigosulfonic acid and other compounds.

Advantageously, this reduction treatment is performed using sodium dithionite as reducing reagent. Alternatively, use may be made of one or other of the following reducing agents: a mixture of arsenic sesquisulfide and of sodium hydrogen sulfite, iron(II) sulfate, zinc, or a reduction by electrolysis may be performed.

Preferably, the reduction treatment is performed in aqueous medium.

Advantageously, the reduction treatment is performed by applying heating at a temperature ranging from 40 to 60° C., advantageously from 45 to 55° C.

Preferably, the total duration of the treatment is from 30 minutes to 6 hours, advantageously from 1 hour to 4 hours.

Preferably, after the reduction treatment, the composition obtained is purified under conditions making it possible to increase the content of leuco-5,5'-indigosulfonic acid. Notably, the medium is extracted with an organic solvent so as to remove certain contaminants, for instance the reduced indigo. The extraction may be performed with ethyl acetate, or with any other solvent that is suitable for extracting non-sulfonated components.

Step iii): Separation of the leuco-5,5'-indigosulfonic Acid

In a second step, the leuco-5,5'-indigosulfonic acid is separated from the reaction medium. Advantageously, the leuco-5,5'-indigosulfonic acid is separated from the reaction medium by precipitation of the leuco-5,5'-indigosulfonic acid, followed by filtration and recovery of the solid.

Preferably, step ii) was performed in a solvent in which the isomer leuco-5,5'-indigosulfonic acid precipitates. Preferably, the isomer leuco-5,5'-indigosulfonic acid is separated from an aqueous composition comprising it. Advantageously, the separation is performed directly in the reaction medium derived from step ii), optionally after a first purification, for instance extraction using an organic solvent. Preferably, the leuco-5,5'-indigosulfonic acid precipitates in the reaction medium on conclusion of step ii).

Alternatively, if the reaction of step ii) was performed in a medium in which leuco-5,5'-indigosulfonic acid is soluble, an addition of water to the reaction medium, or a solvent exchange, may then be performed so as to precipitate the leuco-5,5'-indigosulfonic acid.

Preferably, the separation is performed by passing the reaction medium derived from step ii) through a filtration support. For example, the reaction medium derived from step ii) may be filtered through a filter such as a porosity 3 filter funnel or a multifilament polypropylene filtering gauze. Advantageously, the reaction medium derived from step ii) is hot-filtered, preferably at a temperature ranging from 40 to 60° C., advantageously from 45 to 55° C.

Under these conditions, the isomer leuco-5,5'-indigosulfonic acid, which is solid, is retained by the filter, whereas the other components of the reaction medium, which are soluble in the reaction medium from step ii), are entrained in the aqueous phase during the filtration.

Advantageously, this filtration may be completed with a treatment consisting in slurrying the solid in an organic solvent, for example THF, and filtering the paste thus formed. This slurrying makes it possible to improve the degree of purity of the leuco-5,5'-indigosulfonic acid.

According to the invention, it is advantageously envisaged to complete the leuco-5,5'-indigosulfonic acid separation step by an additional purification such as washing with water, for example by taking up the solid phase comprising the leuco-5,5'-indigosulfonic acid in water, which is brought to a temperature ranging from 40 to 60° C., advantageously from 45 to 55° C., and then filtering the suspension thus prepared. The solid recovered on the filter is leuco-5,5'-indigosulfonic acid. Its degree of purity is improved by this additional purification step.

Advantageously, the operation of washing with water of the leuco-5,5'-indigosulfonic acid is applied from one to five times, even more advantageously from two to four times.

Advantageously, this washing may be completed with a treatment consisting in slurrying the solid in an organic solvent, for instance THF, and filtering the slurry thus formed. This slurrying makes it possible to improve the degree of purity of the leuco-5,5'-indigosulfonic acid.

Advantageously, the purification treatments are repeated until a leuco-5,5'-indigosulfonic acid is obtained which has the expected level of purity. Preferably, the purification treatments are repeated until a composition comprising at least 99 mol % of leuco-5,5'-indigosulfonic acid is obtained, relative to the number of moles of the composition.

Leuco-5,5'-indigosulfonic acid is an essential intermediate in performing the process of the invention.

Use may be made of other techniques, for instance high-pressure liquid chromatography (HPLC), to separate the leuco-5,5'-indigosulfonic acid from the reaction medium derived from step ii). However, filtration has the advantage of being a practical, efficient method that is very readily extrapolable to the industrial scale.

Step iv): Oxidation of leuco-5,5'-indigosulfonic Acid

In a fourth step, leuco-5,5'-indigosulfonic acid is transformed into disodium 5,5'-indigosulfonate via a suitable oxidation treatment, according to scheme 3 below:

Scheme 3: Reduction of leuco-5,5'-indigosulfonic acid to indigo carmine

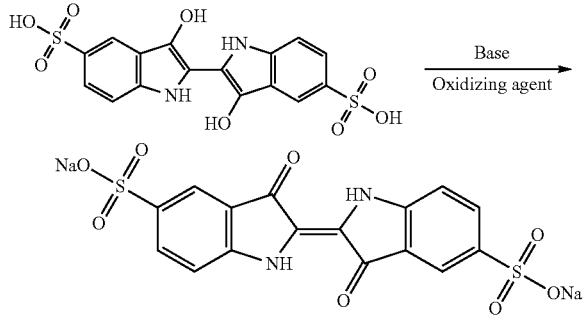

Advantageously, this treatment consists of a treatment with a base in alcoholic medium in the presence of an oxidizing agent. Preferably, the leuco-5,5'-indigosulfonic acid is treated with sodium alkoxide in alcohol medium and in the presence of an oxidizing agent.

Preferably, the leuco-5,5'-indigosulfonic acid is treated with sodium ethoxide in ethanol medium in the presence of an oxidizing agent. Preferably, the treatment is performed hot, advantageously at a temperature ranging from 40 to 60° C., even more advantageously from 45 to 55° C. Preferably, the leuco-5,5'-indigosulfonic acid is treated with 0.5 to 2.5 molar equivalents of sodium alkoxide, preferably 0.8 to 1.5 molar equivalents of sodium alkoxide, in the presence of an oxidizing agent. Even more preferentially, the leuco-5,5'-indigosulfonic acid is treated with 0.5 to 2.5 molar equivalents of sodium ethoxide, preferably 0.8 to 1.5 molar equivalents of sodium ethoxide, in the presence of an oxidizing agent. Advantageously, the oxidizing agent is chosen from $O_2$, $H_2O_2$, $KHSO_5$, $FeCl_3$.

Preferably, the oxidizing agent is gaseous oxygen, which may be used pure or as a mixture with other gases, for instance atmospheric oxygen. Preferably, the duration of the treatment is from 30 minutes to 10 hours, even more preferentially from 1 hour to 8 hours and advantageously from 2 hours to 6 hours.

Preferably, the treatment of step iv) is followed by one or more washes with one or more organic solvents. Preferably, the treatment of step iv) is followed by one or more washes with one or more alcoholic and/or aqueous-alcoholic solvents, notably washing with ethanol and/or washing with methanol and/or washing with a mixture of water and methanol and/or washing with a mixture of water and ethanol.

Uses:

A subject of the invention is also the use of the process described above for producing an indigo carmine or disodium 5,5'-indigosulfonate with a high level of purity. In particular, the invention relates to the use of the process described above for producing a composition comprising at least 99.5%, better still at least 99.7%, of indigo carmine or disodium 5,5'-indigosulfonate. For the evaluation of the amount of indigo carmine in the material composition, the % is measured by high-pressure liquid chromatography (HPLC) with detection at 290 nm, on a 150×4.6 5 µm C18 column, eluting with a gradient of 10 mM sodium phosphate buffer (pH 3.0)+1 mM TBACl/MeOH (70/30→10/90).

The invention relates to the use of the process described above for producing a composition in which no impurity is present in an amount of greater than 0.10%, better still no impurity is present in an amount of greater than 0.05%. The evaluation of the amount of impurities is performed by means of the same method as that used for the evaluation of the amount of indigo carmine.

A subject of the invention is also the use of the process described above for producing a medicament or a diagnostic product comprising indigo carmine or disodium 5,5'-indigosulfonate. Said medicament or diagnostic product may be in any form that is suitable for its use in these applications. In particular, mention may be made of: in the form of a tablet or a gel capsule comprising from 1 to 1000 mg of indigo carmine; in the form of an aqueous solution comprising indigo carmine in a concentration ranging from 0.1% to 10% by mass. Such compositions comprise, besides indigo carmine, excipients that are well known to those skilled in the art, for instance citric acid and/or citrates, a phosphate buffer, polymers, cellulose derivatives, lipids. Formulations comprising indigo carmine are illustrated notably in WO 2011/107945 and in WO 2010/018723. In the medical and diagnostic applications, the indigo carmine obtained via the process of the invention has the advantage of high purity, which avoids the introduction into the body of materials that are not useful for the application.

A subject of the invention is also the use of the process described above for producing a food coloring comprising indigo carmine or disodium 5,5'-indigosulfonate. Said food coloring may be in any form that is suitable for its use in these applications, notably in powder or aqueous solution form. The high level of purity of the indigo carmine obtained via the process of the invention makes it possible to ensure its harmlessness.

The efficiency of the process of the invention affords access to a product with reduced costs.

Experimental Section

I—Materials and Methods:
1—Starting Materials and Equipment:
Indigo was purchased from the company Fisher Scientific under the commercial reference 21213. Purity: 94.8% according to the supplier's specifications.

Gauze (filtration): commercial reference V-05-6-475 K available from the company SEFAR.

Nutsche filter: 280 mm diameter, 35 L, available from the company BUCHI.

2—Analytical Methods:
Machine: Agilent 1100®
Column: KROMASIL C18® 150×4.6-5 µm
Detection: at 290 nm
Concentration of the sample: 1000 ppm
Solvent for dissolving the sample: 90/10 $H_2O$/MeOH
Elution solvent: 10 mM sodium phosphate buffer (pH 3.0)+1 mM TBACl/MeOH II—Protocols:
1—Transformation of Indigo into 5,5'-indigosulfonic Acid:

1.5 kg of indigo (5.72 mol) are placed in a 10 liter reactor, to which are added, with stirring, and at room temperature, 6 liters of aqueous $H_2SO_4$ solution of 96% concentration. The mixture is maintained at 70° C. for 3 hours, with continued stirring. The mixture is then cooled to 5° C. The mixture is added slowly to a 60 liter reactor containing 15 liters of water cooled to 5° C. The addition of the mixture is performed over 1 hour 15 minutes. 90 ml of octanol are added to the mixture and the resulting mixture is brought to 50° C. A solid in suspension in the reaction medium is obtained, which is a mixture comprising 5,5'-indigosulfonic acid.

2—Reduction of the Mixture Comprising 5,5'-indigosulfonic Acid:

An aqueous sodium dithionite solution is prepared from 15 liters of water and 3.51 kg of 85% sodium dithionite solution. The aqueous solution thus prepared is placed in a dropping funnel under nitrogen. The aqueous sodium dithionite solution is added to the reaction mixture obtained from step 1-, with stirring, while maintaining the medium at 50° C. The addition of the aqueous sodium dithionite solution is performed over 1 hour. The mixture is then kept stirring at 50° C. for about 1 hour. 7.5 liters of ethyl acetate are then added to the mixture, and the resulting mixture is stirred at 50° C. for 20 minutes. The medium is still in the form of a suspension comprising leuco-5,5'-indigosulfonic acid.

3—Separation of the leuco-5,5'-indigosulfonic Acid:

The reaction medium derived from step 2—is then filtered through a Nutsche filter, equipped with a V-05-6-475 K gauze.

The solid remaining on the filter is slurried with 4.5 liters of tetrahydrofuran (THF) and the liquid is then filtered.

4—Washing of the leuco-5,5'-indigosulfonic Acid:

The product remaining on the filter on conclusion of step 3—is taken up in 30 liters of water, in a 60 liter reactor. The whole is heated at 50° C. for 30 minutes and then filtered through the Nutsche filter, equipped with a V-05-6-475 K gauze.

The solid remaining on the filter is slurried with 4.5 liters of tetrahydrofuran (THF) and the liquid is then filtered.

This washing is repeated so as to arrive at a total of three washes under the same conditions. 1.8 kg of a wet product are obtained. Estimated dry mass: 1.3 kg.

5—Transformation of the Disodium leuco-5,5'-indigosulfonate Acid into Disodium 5,5'-indigosulfonate The 1.8 kg of product obtained in step 4—are suspended in 26 liters of ethanol in a 60 liter reactor. 1143 ml of a solution containing 21% by mass of sodium ethoxide (NaOEt) in ethanol are added. The mixture is brought to 50° C. and air is sparged into the reaction medium over 4 hours, while maintaining it at 50° C.

At the end of this period, the reaction medium is filtered through a sinter funnel, the filtration being followed by washing with 5.2 liters of ethanol.

6—Washing of the Disodium 5,5'-indigosulfonate

The wet solid is taken up in 26 liters of methanol, the whole is heated for 30 minutes at 40° C. and then filtered through a sinter funnel, the filtration being followed by washing with 5.2 liters of methanol.

This washing is repeated once.

Next, the wet solid is taken up in a mixture of 13 liters of water and 13 liters of methanol, the whole is heated for 30 minutes at 60° C. and then filtered through a sinter funnel, the filtration being followed by washing with 3.9 liters of methanol.

The solid is dried in a ventilated oven.

1.05 kg of disodium 5,5'-indigosulfonate are obtained, the yield is 39% relative to the total amount of indigo engaged in the process.

III—Results:

The product obtained is analyzed by HPLC by means of the method described above. The purity is evaluated as being from 99.85% to 99.95%, as a function of the tests (three tests performed).

It is found that the process of the invention makes it possible to obtain a product of high purity, with good yields, by applying a simple, inexpensive protocol that is easily extrapolable to large scale, and with results that are reproducible from the point of view of the quality (purity) of the product obtained.

The invention claimed is:

1. A process for preparing disodium 5,5'-indigosulfonate, the starting material being indigo, this process comprising the following steps:
   i) indigo is subjected to a sulfonation treatment leading to a mixture which contains 5,5'-indigosulfonic acid,
   ii) the mixture obtained in step i) is subjected to a reduction treatment, and optionally a purification step, so as to obtain a composition comprising leuco-5,5'-indigosulfonic acid,
   iii) the leuco-5,5'-indigosulfonic acid is isolated from the composition derived from step ii) and,
   iv) the leuco-5,5'-indigosulfonic acid obtained from step iii) is oxidized to disodium 5,5'-indigosulfonate.

2. The process as claimed in claim 1, in which the reduction treatment of step ii) is performed using sodium dithionite in aqueous medium.

3. The process as claimed in claim 1, in which the leuco-5,5'-indigosulfonic acid precipitates in the reaction medium on conclusion of step ii).

4. The process as claimed in claim 1, in which step iii) includes the steps of:
   iiia) filtration of the composition obtained from step ii) and,
   iiib) recovery of the solid retained on the filter.

5. The process as claimed in claim 4, in which step iii) also includes, after step iiib), at least one step iiic) consisting of washing the solid with an aqueous medium.

6. The process as claimed in claim 5, in which step iiic) is applied from one to five times.

7. The process as claimed in claim 1, in which the composition obtained on conclusion of step iii) includes at least 90 mol % of leuco-5,5'-indigosulfonic acid relative to the total number of moles of the composition.

8. The process as claimed in claim 1, in which step iv) includes at least one step iva) consisting of a treatment with a base in alcoholic medium in the presence of an oxidizing agent.

9. The process as claimed in claim 8, in which step iva) consists of a treatment with sodium ethoxide in ethanol, in the presence of an oxidizing agent.

10. The process as claimed in claim 8, in which the oxidizing agent is gaseous oxygen.

11. The process as claimed in claim 8, which also includes, after step iva), at least one step ivb) consisting of one or more washes with one or more alcoholic and/or aqueous-alcoholic solvents.

12. The process as claimed in claim 1 wherein the process produces a composition comprising at least 99.5% of disodium 5,5'-indigosulfonate, the percentage being measured by high-pressure liquid chromatography with detection at 290 nm.

13. The process as claimed in claim 1 wherein the process produces a composition in which no impurity is present in an amount of greater than 0.10%, the percentage being measured by high-pressure liquid chromatography with detection at 290 nm.

14. A process of manufacturing a medicament or a diagnostic product comprising disodium 5,5'-indigosulfonate, this process comprising manufacturing of disodium 5,5'-indigosulfonate via the process as claimed in claim 1 and the introduction of the disodium 5,5'-indigosulfonate into a pharmaceutically acceptable support.

15. A process of manufacturing a food composition comprising disodium 5,5'-indigosulfonate, this process comprising manufacturing of disodium 5,5'-indigosulfonate via the process as claimed in claim 1 and the introduction of the disodium 5,5'-indigosulfonate into a support that is compatible with a food application.

* * * * *